(12) United States Patent
Martinez et al.

(10) Patent No.: US 10,347,383 B2
(45) Date of Patent: Jul. 9, 2019

(54) PROCESS FOR PREPARING A METAL OXIDE POWDER, PROCESS FOR MANUFACTURING A METAL OXIDE PELLET, POWDER AND PELLET AS OBTAINED ACCORDING TO THESE PROCESSES AND USES THEREOF

(71) Applicants: COMMISSARIAT A L'ENERGIE ATOMIQUE ET AUX ENERGIES ALTERNATIVES, Paris (FR); Orano Cycle, Courbevoie (FR)

(72) Inventors: Julien Martinez, Uzes (FR); Fabienne Audubert, Cadenet (FR); Nicolas Clavier, Sauveterre (FR); Nicolas Dacheux, Rochefort du Gard (FR)

(73) Assignees: Commissariat a L'Energie Atomique et al Energies Alternatives, Paris (FR); Orano Cycle, Courbevoie (FR)

( * ) Notice: Subject to any disclaimer, the term of this patent is extended or adjusted under 35 U.S.C. 154(b) by 59 days.

(21) Appl. No.: 15/110,497

(22) PCT Filed: Jan. 14, 2015

(86) PCT No.: PCT/EP2015/050603
§ 371 (c)(1),
(2) Date: Jul. 8, 2016

(87) PCT Pub. No.: WO2015/107086
PCT Pub. Date: Jul. 23, 2015

(65) Prior Publication Data
US 2016/0329112 A1 Nov. 10, 2016

(30) Foreign Application Priority Data

Jan. 14, 2014 (FR) ..................... 14 50276

(51) Int. Cl.
*C01G 1/02* (2006.01)
*G21C 3/62* (2006.01)
(Continued)

(52) U.S. Cl.
CPC .............. *G21C 3/623* (2013.01); *C01F 15/00* (2013.01); *C01F 17/0043* (2013.01); *C01G 1/02* (2013.01);
(Continued)

(58) Field of Classification Search
CPC .......... C01G 1/02; C01G 25/02; C01G 27/02; C01G 43/025; C01G 56/00; C01G 56/005; C01G 56/008; G21C 3/623
See application file for complete search history.

(56) References Cited

U.S. PATENT DOCUMENTS 3,262,760 A 7/1966 Morse et al.
3,287,279 A 11/1966 Lyon
(Continued)

FOREIGN PATENT DOCUMENTS

BE 657170 A 4/1965
CH 478442 A 9/1969
(Continued)

OTHER PUBLICATIONS

Hingant, N., et al., "Preparation, sintering and leaching of optimized uranium thorium dioxides", Journal of Nuclear Materials, Dec. 7, 2008, pp. 400-406, vol. 385.
(Continued)

Primary Examiner — Kelly M Gambetta
(74) Attorney, Agent, or Firm — Alston & Bird LLP

(57) ABSTRACT

A process is provided for preparing a powder of an oxide of at least one metal, each metal having an oxidation number between (III) and (VI). This process comprises successively and in this order:
(Continued)

(a) reacting, with a compound comprising a hydroxide, an aqueous solution comprising, for each metal, at least one salt of the cation of said metal,
(b) separating the precipitate obtained,
(c) contacting the separated precipitate with an organic protic polar solvent,
(d) removing the organic protic polar solvent by vacuum drying the precipitate.

A process is further provided for manufacturing a pellet of an oxide of at least one metal as well as to a powder and to a pellet obtained according to these processes and to uses thereof.

22 Claims, 9 Drawing Sheets

(51) Int. Cl.
| | | |
|---|---|---|
| *C01G 25/02* | (2006.01) | |
| *C01G 27/02* | (2006.01) | |
| *C01G 56/00* | (2006.01) | |
| *C01G 43/025* | (2006.01) | |
| *C01F 17/00* | (2006.01) | |
| *C01F 15/00* | (2006.01) | |
| *G01N 27/407* | (2006.01) | |
| *G21C 21/02* | (2006.01) | |
| *H01M 8/1246* | (2016.01) | |
| *H01M 8/126* | (2016.01) | |
| *H01M 8/124* | (2016.01) | |

(52) U.S. Cl.
CPC ............ *C01G 25/02* (2013.01); *C01G 27/02* (2013.01); *C01G 43/025* (2013.01); *C01G 56/00* (2013.01); *C01G 56/005* (2013.01); *C01G 56/008* (2013.01); *G01N 27/4073* (2013.01); *G21C 21/02* (2013.01); *H01M 8/126* (2013.01); *H01M 8/1246* (2013.01); *C01P 2002/72* (2013.01); *C01P 2004/03* (2013.01); *C01P 2004/50* (2013.01); *C01P 2004/62* (2013.01); *C01P 2004/64* (2013.01); *C01P 2006/12* (2013.01); *H01M 2008/1293* (2013.01); *Y02E 30/38* (2013.01)

(56) References Cited

U.S. PATENT DOCUMENTS

| | | | |
|---|---|---|---|
| 3,923,933 A | | 12/1975 | Lay |
| 3,963,828 A | * | 6/1976 | Becker ................. C01G 43/025 252/636 |
| 4,314,952 A | | 2/1982 | Zawidzki |
| 4,382,885 A | * | 5/1983 | Haas .......................... B01J 2/08 252/634 |
| 4,971,734 A | * | 11/1990 | Floreancig .......... C01B 15/0475 252/5 |
| 5,391,347 A | | 2/1995 | Bastide et al. |

FOREIGN PATENT DOCUMENTS

| | | |
|---|---|---|
| CN | 1636879 A | 7/2005 |
| CN | 1850621 A | 10/2006 |
| EP | 0351334 A1 | 1/1990 |
| EP | 0491635 A1 | 6/1992 |
| FR | 1489438 A | 7/1967 |
| FR | 2424231 A1 | 11/1979 |
| GB | 1128838 A | 10/1968 |
| JP | 2005/170775 A | 6/2005 |
| JP | 2007-169085 A | 7/2007 |
| JP | 2009-274897 A | 11/2009 |

OTHER PUBLICATIONS

Yiru, T., et al., "Preparation of Uranium Dioxide Powder: Process for Production of Coarse Particle ADU Precipitation in Pilot Plant", "China Nuclear Science and Technology Report", Oct. 31, 1989, pp. 1-7, vol. S3.

* cited by examiner

PROCESS FOR PREPARING A METAL OXIDE POWDER, PROCESS FOR MANUFACTURING A METAL OXIDE PELLET, POWDER AND PELLET AS OBTAINED ACCORDING TO THESE PROCESSES AND USES THEREOF

CROSS-REFERENCE TO RELATED APPLICATIONS

This application is a U.S. national phase under the provisions of 35 U.S.C. § 371 of International Patent Application No. PCT/EP15/50603 filed Jan. 14, 2015, which in turn claims priority of French Patent Application No. 1450276 filed Jan. 14, 2014. The disclosures of such international patent application and French priority patent application are hereby incorporated herein by reference in their respective entireties, for all purposes.

TECHNICAL FIELD

The present invention relates to a process for preparing a powder of a metal oxide, this metal oxide being an oxide of at least one metal which has an oxidation number between (III) and (VI).

It also relates to a process for manufacturing a pellet of a metal oxide from the powder of metal oxide as prepared by the abovementioned process.

The invention enables a powder of a metal oxide with a strong reactivity as well as a pellet of a metal oxide to be obtained. These strong reactivity properties are closely related to the particle size of the particles forming the powder of the metal oxide prepared according to the process of the invention, this powder having a very high specific surface area.

The powder obtained can be a powder of a single metal oxide such as a powder of uranium oxide or cerium oxide, or even a powder of a mixed metal oxide such as a powder of a uranium and cerium mixed oxide, a cerium and gadolinium mixed oxide or a uranium and plutonium mixed oxide.

The powder as well as the pellet as obtained by the processes according to the invention can be used in numerous fields and, in particular, in the field of nuclear industry or even in the field of ionic conductors.

STATE OF PRIOR ART

Among the actinides and/or lanthanides oxides used in the field of nuclear industry, uranium dioxide $UO_2$ as well as some uranium based mixed oxides, such as the uranium and plutonium mixed oxide $(U,Pu)O_2$ or even the uranium and thorium mixed oxide $(U,Th)O_2$, are part of the most commonly used metal mixed oxides for manufacturing nuclear fuels.

These single or mixed metal oxides are conventionally in the form of compacted and sintered pellets, which have to meet a number of requirements imposed by the nuclear industry. Among these requirements, such pellets of nuclear fuel must have a high density, typically equal to or higher than 95%.

The final density of the pellet is in particular a function of properties of the powder of metal oxide from which the pellet is obtained, in particular of the reactivity of said powder. It is also a function of other parameters of the powder such as homogeneity, the absence of impurities, and the process parameters such as sintering parameters.

The reactivity, being a property related to the specific surface area of the particles of the powder forming the pellets, many researches have consequently been conducted to provide a process for manufacturing nuclear fuel pellets comprising particles of metal oxide the average diameter of which is as low as possible.

Conventionally, the processes for manufacturing nuclear fuel pellets include several successive steps made from an aqueous solution of soluble salts of the metal(s) present in the powder of metal oxide being part of the composition of the nuclear fuel pellets. Such soluble metal salts generally consist of nitrates or sulphates of the metal(s) considered.

Thus, document GB 1,128,838, referenced as [1] at the end of the present description, describes a process for preparing fuel elements of uranium and plutonium oxides usable in nuclear reactors. In this process, uranium and plutonium are co-precipitated from an aqueous solution quickly and in a form enabling them to be filtered, and then dried. More particularly, the process described in document [1] comprises successively and in this order:

(a) contacting, with ammonium hydroxide, a solution of uranyl nitrate and plutonium nitrate, in a uranium and plutonium molar concentration ratio close to one, leading to the co-precipitation of an intimate mixture of uranium diuranate and plutonium hydrous oxides, (b) filtering the precipitate on a conventional filtering apparatus, (c) washing several times, with water and acetone, the filtered precipitate, (d) air drying the washed precipitate, and then (e) reducing, under a reducing atmosphere comprising dihydrogen, at a temperature between 600° C. and 900° C., the dried precipitate for converting the compounds comprising uranium and plutonium into a powder of uranium and plutonium oxides, this powder being readily sinterable.

According to document [1], this powder can be passed through a ball mill and then through a sieve "having 325 openings per linear inch", also indicating that the diameter of the particles forming the powder of uranium and plutonium oxides obtained is in the order of a few tens of micrometers.

The process described in document [1] can also comprise a further step of compacting under high pressure the powder obtained at the end of step (e), followed by a sintering step for obtaining pellets of uranium and plutonium oxides.

The major drawback of the preparing process described in document [1] lies in the relatively high number of successive steps that it includes. Furthermore, this process implements a reducing step (e) which, being conducted at temperatures between 600° C. and 900° C., is energy-consuming, as well an additional milling step for obtaining a diameter of particles making up the powder which is as low as possible.

Document U.S. Pat. No. 4,314,952, referenced as [2], relates to a process for manufacturing pellets of uranium dioxide $UO_2$ intended to be used in nuclear reactors, these pellets having a high mass density as well as a size of its constituent particles being higher than 50 µm and, advantageously, between about 50 µm and 1 000 µm. The process described in document [2] comprises successively and in this order:

(a) contacting a uranyl nitrate with a sulphur source, generally sulphuric acid, at a temperature between 300° C. and 400° C., leading to a sulphur containing uranium trioxide, (b) contacting, with ammonium nitrate, this uranium trioxide, leading to a suspension comprising a sulphur containing insoluble ammonium uranate,
(c) contacting, with ammonium hydroxide, this suspension, to precipitate uranium remained in solution as insoluble ammonium uranate,
(d) recovering and then drying the ammonium uranate,
(e) reducing the dried ammonium uranate into uranium dioxide $UO_2$,
(f) compacting the uranium dioxide as pellets, and then
(g) sintering said pellets, under a dihydrogen atmosphere, at a high temperature.

In addition to involving a relatively high number of steps including a reducing step conducting at a high temperature, the process for manufacturing uranium dioxide pellets described in document [2] has, as another major drawback, to produce sulphur containing compounds.

Document U.S. Pat. No. 4,382,885, referenced as [3], also relates to the manufacture of nuclear fuels having the form of pellets, these pellets being themselves formed by sintered spheres. These sintered spheres are made of a fissile material and have a diameter in the order of 100 μm to 1 000 μm. The process therefor includes not less than ten steps, including a step of forming droplets by passing a sieved suspension through a nozzle. More precisely, the suspension is formed by a solution of one or more actinide salts in the presence of a reagent chosen from ammonium hydroxide, ammonium oxalate, oxalic acid and a mixture of these compounds. These suspension droplets are then contacted with ammonia gas and then with a concentrated ammonium hydroxide solution to transform, by gelling, said droplets into solidified spheres. After washing and drying in an oven at a temperature between 150° C. and 400° C., the dried spheres are then calcined at a temperature between 400° C. and 800° C., compacted as pellets which are then sintered at a temperature between 1450° C. and 1700° C.

The process described in document [3] is characterized by an excessively high number of steps, some of which, as those consisting in forming the droplets by means of the nozzle and then contacting these droplets with ammonia gas to form gelled spheres, are of a particularly complex implementation.

Document U.S. Pat. No. 4,971,734, referenced as [4], describes a process for obtaining nuclear fuel pellets of sintered oxides having the formula $M_xO_y$, M representing one or more chemical elements conventionally used in manufacturing nuclear fuel pellets, such as uranium, plutonium, thorium, cerium, gadolinium or even hafnium.

The process described in document [4] comprises successively and in this order:
(a) treating, by hydrogen peroxide and ammonia, a solution comprising one or more salts of the element(s) M, leading to a peroxide precipitate,
(b) filtering the precipitate,
(c) calcining the filtered precipitate,
(d) reducing, in an oven, the calcined precipitate, leading to an intermediate powder of oxides, and then
(e) pressing the intermediate powder, and then
(f) sintering the pressed intermediate powder leading to obtaining sintered oxide pellets having a very strong density, generally higher than 96%.

Although document [4] describes that an intermediate powder, formed by spherical particles having a controlled narrow size particle, is obtained without additional milling, sieving and/or granulating step, it however indicates that this intermediate powder is "released from conglomerates which may have formed during heat treatments".

As all the above processes, the process of document [4] implements particularly energy-consuming steps, that is a calcining step as well as a reducing step.

The purpose of the invention is consequently to overcome the drawbacks of prior art and to provide a process for preparing a powder of an oxide of at least one metal, each metal having an oxidation number between (III) and (VI), in particular (III), (IV) and/or (VI) and, in particular, (III) and/or (IV), enabling a powder to be obtained, having a strong reactivity and a particle size as fine as possible and, in particular, an average particle diameter equal to or lower than 1 μm and, advantageously, equal to or lower than 100 nm in a reduced number of steps with respect to that of preparing processes of prior art, as those described in documents [1] to [3]. In particular, this process should enable such a particle size to be achieved, in the absence of a milling step.

This process should further enable a powder of such an oxide of at least one metal to be obtained in the absence of particularly heat energy-consuming steps, such as a drying step at more than 100° C., a calcining step and/or a reducing step.

More generally, the process according to the invention has to be as direct as possible and should allow for an industrial implementation which is technically and economically optimized.

DISCLOSURE OF THE INVENTION

The purposes mentioned previously, as well as others are achieved, firstly, by a process for preparing a powder of an oxide of at least one metal, each metal having an oxidation number between (III) and (VI).

It is specified that the phrase "between . . . and . . . " just mentioned and which is used in the present application has to be understood as defining not only the values of the interval, but also the values of the limits of this interval.

Thus, the process enables to prepare a powder of an oxide of at least one metal, each metal having an oxidation number of (III), (IV), (V) and/or (VI), in particular (III), (IV) and/or (VI) and, in particular, (III) and/or (IV).

According to the invention, this process comprises successively and in this order:
(a) reacting, with a compound comprising a hydroxide, an aqueous solution comprising, for each metal, at least one salt of the cation of said metal, leading to a precipitate of the hydrated oxide of said at least one metal,
(b) separating the precipitate obtained,
(c) contacting the separated precipitate with an organic protic polar solvent,
(d) removing the organic protic polar solvent by vacuum drying the precipitate, leading to the powder of the hydrated oxide of said at least one metal, said powder being formed of particles the average diameter of which is equal to or lower than 1 μm.

The process according to the invention thus enables a powder of a metal oxide having a strong reactivity to be obtained, in a particularly restricted number of steps, unlike processes of prior art such as those described in documents [1] to [3].

More particularly, the process according to the invention enables this powder of a metal oxide to be obtained with a particularly fine particle size, in the absence of further steps of reducing, drying at a relatively high temperature (typically higher than 100° C.), calcining and/or milling.

Obtaining this powder with such a particle size results from the particular combination of steps (a) to (d) of the process and, in particular, as will be seen hereinafter, from the choice of a compound comprising a hydroxide as a reagent enabling the hydrated metal oxide to be precipitated and of a step of vacuum drying this hydrated metal oxide placed beforehand in an organic protic polar solvent.

As is clearly apparent from the detailed disclosure of particular embodiments described hereinafter, the inventors have observed that, when the aqueous solution, which comprises, for each metal, at least one salt of the cation of said metal, reacts with a compound comprising a hydroxide, a precipitate of a hydrated hydroxide of said at least one metal is firstly formed. However, this precipitate of a hydrated metal hydroxide being a particularly reactive compound, it spontaneously changes to be transformed into a precipitate of the hydrated oxide of said at least one metal, given that this hydrated metal oxide itself gradually changes from an amorphous structure to a crystalline structure. This transformation of the hydrated metal hydroxide into a hydrated metal oxide occurs in the absence of a modification of the physicochemical properties of the precipitate, which maintains, in particular, its reactivity.

After separating, for example by filtration or centrifugation, the precipitate formed by this hydrated metal oxide, the latter is contacted, during step (c), with an organic protic polar solvent, which is then removed by vacuum drying. By virtue of this particular step (d), the organic protic polar solvent is gradually removed. Furthermore, the suspension formed by the precipitate of a hydrated metal oxide and the organic protic polar solvent undergoes a homogeneous cooling, which enables to maintain the reactivity of the powder of a hydrated metal oxide to be maintained and to avoid an agglomeration of the particles forming this powder. Furthermore, the vacuum drying enables the organic protic polar solvent either to be more quickly removed than a simple air drying, or to be removed under lower temperature conditions than those which can be implemented during a drying in an oven. However, it may be contemplated, during this vacuum drying step (d), to slightly heat the suspension formed by the precipitate of hydrated metal oxide and the organic protic polar solvent. Of course, the vacuum applied for this drying step is suitable for the organic protic polar solvent chosen and, in particular, for its saturating vapour pressure value.

The inventors have also highlighted the existence of a real synergy occurring between the choice of the reagent, that is a compound comprising a hydroxide, and that of the particular contacting (c) and drying (d) steps since they allow for contemplating drying the powder of a hydrated metal oxide which does not agglomerate. But, as will be seen in the examples 1 and 4 hereinafter, when another reagent, that is oxalic acid, is chosen, the particles of metal oxide powder as obtained remain agglomerated together, regardless of the drying conditions of said powder.

According to an advantageous alternative of the process according to the invention, the powder of the hydrated oxide of said at least one metal is formed by particles the average diameter of which is equal to or lower than 100 nm, advantageously equal to or lower than 20 nm and, preferably, equal to or lower than 10 nm.

According to another advantageous alternative of the process according to the invention, the powder of the hydrated oxide of said at least one metal has a specific surface area, measured according to the BET method, equal to or higher than 30 $m^2/g$, advantageously equal to or higher than 80 $m^2/g$ and, preferably, equal to or higher than 100 $m^2/g$.

These specific surface area values, which reflect the reactivity of the powder of the hydrated metal oxide, are much higher than those of a powder of a comparable hydrated metal oxide which is prepared by the implementation of steps (a) to (c) identical to those of the process according to the invention, but with a step (d) of removing the organic protic polar solvent performed by air drying.

According to another advantageous alternative of the process according to the invention, the process further comprises, after step (b) and before step (c), a step of washing the precipitate of the hydrated oxide of said at least one metal which has been separated, for example by filtration or by centrifugation, during step (b).

This washing can be made by passing one or more times a same solvent or different solvents, this(these) solvent(s) being preferably protic solvents, optionally in mixture with water.

This washing can in particular be made by ethanol or even by a water and ethanol mixture. When water is employed for this step of washing the precipitate of the hydrated metal oxide hydrated, deionized water is preferably used.

According to another advantageous alternative of the process according to the invention, the process further comprises, after step (d):
  (e) heat treating the powder of the hydrated oxide of said at least one metal, leading to the powder of the anhydrous oxide of said at least one metal.

Thus, during this step (e), under the effect of the heat treatment of the powder obtained at the end of the step (d), the full dehydration of the hydrated metal oxide into the corresponding anhydrous metal oxide occurs.

It is set forth that a partial dehydration of the hydrated metal oxide also occurs during step (d) per se, that is during the removal of the organic protic polar solvent by vacuum drying.

As already mentioned previously, in the process for preparing a powder of an oxide of at least one metal according to the invention, each metal has an oxidation number between (III) and (VI), in particular (III), (IV) and/or (VI) and, in particular, (III) and/or (IV).

According to an advantageous alternative of the invention, each metal is chosen from actinides, lanthanides and transition metals, these metals having necessarily an oxidation number between (III) and (VI), in particular (III), (IV) and/or (VI) and, in particular, (III) and/or (IV).

When the metal is an actinide, it is advantageously chosen from a chemical element of the group consisting of uranium U, thorium Th, plutonium Pu, neptunium Np, americium Am and curium Cm.

When the metal is a lanthanide, it is advantageously chosen from a chemical element of the group consisting of cerium Ce, gadolinium Gd, neodymium Nd, samarium Sm and europium Eu.

When the metal is a transition metal, it is advantageously chosen from a chemical element of the group consisting of titanium Ti, chromium Cr, zirconium Zr, scandium Sc, yttrium Y and hafnium Hf.

By way of examples, the metal can advantageously be chosen from a chemical element of the group consisting of U(IV), U(VI), Th(IV), Pu(III), Pu(IV), Pu(VI), Am(III), Np(IV), Np(VI), Ce(III), Ce(IV), Gd(III), Nd(III) and Zr(IV).

The process according to the invention relates to the preparation of a powder of an oxide of at least one metal, each metal having an oxidation number between (III) and (VI), in particular (III), (IV) and/or (VI) and, in particular, (III) and/or (IV).

Thus, according to a first embodiment of the invention, the process enables a powder of an oxide of a single metal, also called single oxide, to be prepared. This powder of an oxide of a single metal can thus be in particular a powder of an actinide oxide, a lanthanide oxide or a transition metal oxide.

Such a single oxide is, preferably, chosen from uranium dioxide $UO_{2+\delta}$, uranium trioxide $UO_3$, triuranium octaoxide $U_3O_8$, cerium dioxide $CeO_{2-\delta}$, thorium dioxide $ThO_2$, plutonium dioxide $PuO_{2-\delta}$, neptunium dioxide $NpO_{2+\delta}$, zirconium dioxide $ZrO_2$ and hafnium dioxide $HfO_2$. The $\delta$ value is variable as a function of the metal making up the oxide considered. Typically, $\delta$ is between 0 and 0.5, the value of 0 being included and the value of 0.5 being excluded ($0 \leq \delta < 0.5$).

According to a second embodiment of the invention, the process also enables a powder of an oxide of two, three or even more metals, also called a mixed oxide, to be prepared. This powder of an oxide of two, three or more metals can thus be in particular a powder of an actinides mixed oxide, a lanthanides mixed oxide or a transition metals mixed oxide. It can also be a powder of an actinide(s) and lanthanide(s) mixed oxide, an actinide(s) and transition metal(s) mixed oxide, a lanthanide(s) and a transition metal(s) mixed oxide or even an actinide(s), lanthanide(s) and transition metal(s) mixed oxide.

Such a mixed oxide is preferably chosen from a uranium and cerium mixed oxide $(U,Ce)O_{2\pm\delta}$, a uranium and plutonium mixed oxide $(U,Pu)O_{2\pm\delta}$, a uranium and americium mixed oxide $(U,Am)O_{2\pm\delta}$, a uranium and thorium mixed oxide $(U,Th)O_{2+\delta}$, a cerium and gadolinium mixed oxide $(Ce,Gd)O_{2-\delta}$, a uranium and gadolinium mixed oxide $(U,Gd)O_{2\pm\delta}$, a thorium and plutonium mixed oxide $(Th,Pu)O_{2-\delta}$, a thorium and yttrium mixed oxide $(Th,Y)O_{2-\delta}$ and a uranium, plutonium and americium mixed oxide $(U,Pu,Am)O_{2\pm\delta}$. The value of $\delta$ is variable as a function of the metals making up the mixed oxide considered. Typically, $\delta$ is between 0 and 0.5, the value of 0 being included and the value of 0.5 being excluded ($0 \leq \delta < 0.5$).

It is set forth that at the end of step (d), the powder of the oxide of said at least one metal which is obtained, regardless of whether this oxide is a single oxide or a mixed oxide, is a powder of the metal oxide in a hydrated form, commonly noted $nH_2O$.

According to an advantageous alternative of the invention, in step (a), for each metal, the salt of the cation said metal is chosen from a sulphate, nitrate, halide, given that this cation can be trivalent, tetravalent, pentavalent and/or hexavalent. When this salt is a halide, a chloride or a bromide can advantageously be used.

For the purposes of the present invention, the compound comprising a hydroxide which is used as a reagent in step (a) of the process is a compound which comprises at least one hydroxide anion $OH^-$ and at least one cation, so as to ensure electronneutrality of said compound.

By way of example, the cation of the compound comprising a hydroxide can be a primary, secondary or tertiary ammonium, or simply be the ammonium cation $NH_4^+$. The cation can also be the hydrazinium cation $N_2H_5^+$.

The cation of the compound comprising a hydroxide can also be a metal cation, in particular an alkaline metal cation, such as sodium Na or potassium K, or an alkaline earth metal cation, such as calcium Ca or magnesium Mg.

The compound comprising a hydroxide can thus be chosen from ammonium hydroxide $NH_4OH$, hydrazinium hydroxide $N_2H_5OH$, sodium hydroxide NaOH, potassium hydroxide KOH, calcium hydroxide $Ca(OH)_2$ or even magnesium hydroxide $Mg(OH)_2$.

The compound comprising a hydroxide can also originate from a compound enabling the anion $OH^-$ to be formed in an aqueous solution. By way of example, the compound comprising an ammonium cation $NH_4^+$ and a hydroxide anion $OH^-$ can originate from either from the ammonium hydroxide $NH_4OH$ as a salt, or from the reaction product of ammonia $NH_3$ in water.

According to an advantageous alternative of the invention, in step (a), the compound comprising a hydroxide is ammonium hydroxide $NH_4OH$ or hydrazinium hydroxide $N_2H_5OH$.

According to an advantageous alternative of the invention, in step (a), the molar content of the compound comprising a hydroxide is in excess with respect to the total molar content of cation(s) of said at least one metal having an oxidation number between (III) and (VI). It is set forth that this(these) cation(s) are trivalent, tetravalent, pentavalent and/or hexavalent, as a function of the oxidation number of said metal considered. This molar content of the compound comprising a hydroxide is advantageously between 150% and 600% and, preferably, between 300% and 500%, with respect to the total molar content of cation(s) of said at least one metal.

According to an advantageous alternative of the invention, in step (c), the organic protic polar solvent is chosen from a carboxylic acid, a primary amine and an alcohol.

When the organic protic polar solvent is a carboxylic acid, this carboxylic acid can in particular be chosen from formic acid, acetic acid and propionic acid.

When the organic protic polar solvent is a primary amine, this primary amine can in particular be chosen from methylamine, ethylamine and isopropylamine.

When the organic protic polar solvent is an alcohol, this alcohol can in particular be a monoalcohol or diol. Such an alcohol is, preferably, chosen from the group consisting of methanol, ethanol and ethanediol.

According to an advantageous alternative of the invention, in step (d), the vacuum drying is made by means of a vacuum manifold, the vacuum manifold making it possible both to create a vacuum in the internal space of the flask, comprising the suspension formed by the precipitate of the hydrated metal oxide and the organic protic polar solvent, and to release this vacuum, by introducing in the same flask, a gas, in particular an inert gas such as dinitrogen, argon or helium. Alternatively, a reducing gas can be introduced.

In order to promote the evaporation of the organic protic polar solvent of the suspension and obtain the powder of the hydrated metal oxide at its driest form, it is particularly advantageous to heat and/or keep, under steering, the suspension formed by the precipitate of the hydrated metal oxide and the organic protic polar solvent.

The invention relates, secondly, to a powder of an oxide of at least one metal, each metal having an oxidation number between (III) and (VI), in particular (III), (IV) and/or (VI) and, in particular, (III) and/or (IV), obtained by the implementation of the preparing process as defined above, wherein the advantageous characteristics of this process can be taken alone or in combination.

The invention relates, thirdly, to different uses of such a powder of an oxide of at least one metal, each metal having an oxidation number between (III) and (VI), in particular (III), (IV) and/or (VI) and, in particular, (III) and/or (IV).

According to the invention, this powder of an oxide of at least one metal can be used for manufacturing nuclear fuel.

According to the invention, this powder of an oxide of at least one metal can also be used as a catalyst support.

According to the invention, this powder of an oxide of at least one metal, when this metal is uranium, can also be used for preparing triuranium octaoxide $U_3O_8$.

According to the invention, this powder of an oxide of at least one metal can also be used in a hydrofluorination process.

According to the invention, this powder of an oxide of at least one metal can also be used for manufacturing an ionic conductor, such as a solid electrolyte for a solid oxide fuel cell (SOFC) or an oxygen measuring probe.

According to the invention, this powder of an oxide of at least one metal can also be used for manufacturing ceramics. Such a ceramics, also called "oxide ceramics", can in particular be used as a nuclear fuel pellet or as an ionic conductor, this ionic conductor possibly being a solid electrolyte for a SOFC cell or an oxygen measuring probe, as previously mentioned.

The invention relates, fourthly, to a process for manufacturing a pellet of an oxide of at least one metal, each metal having an oxidation number between (III) and (VI), in particular (III), (IV) and/or (VI) and, in particular, (III) and/or (IV).

According to the invention, this process comprises successively and in this order:
(1) preparing a powder of an oxide of at least one metal, each metal having an oxidation number between (III) and (VI), by implementing the process as defined above, the advantageous characteristics of this process possibly being taken alone or in combination,
(2) compacting the powder, and
(3) heat treating the compacted powder, leading to the pellet of the oxide of at least one metal.

In other words, the process for manufacturing a pellet of an oxide of at least one metal, each metal having an oxidation number between (III) and (VI), comprises successively and in this order:
(a) reacting, with a compound comprising a hydroxide, an aqueous solution comprising, for each metal, at least one salt of the cation of said metal, leading to a precipitate of the hydrated oxide of said at least one metal,
(b) separating the precipitate obtained,
(c) contacting the separated precipitate with an organic protic polar solvent,
(d) removing the organic protic polar solvent by vacuum drying the precipitate, leading to a powder of the hydrated oxide of said at least one metal, said powder being formed of particles the average diameter of which is equal to or lower than 1 µm,
(e) compacting the powder, and
(f) heat treating the compacted powder, leading to the pellet of the oxide of at least one metal.

The process according to the invention thus makes it possible to obtain a pellet of a metal oxide having a high density in a particularly restricting number of steps, unlike processes of prior art such as those described in documents [1] to [3].

Further, this pellet of a metal oxide as obtained according to the process according to the invention has a very good mechanical strength, which is an obvious advantage for the subsequent handling of such a pellet.

According to an advantageous alternative of the process according to the invention, the pellet of an oxide of at least one metal has a density of at least 90% and, advantageously, of at least 95%.

According to another advantageous alternative of the process according to the invention, step (3), or (f), of heat treatment, is made by applying a temperature gradient extending from room temperature to a temperature equal to or lower than 1600° C. and, advantageously, equal to or lower than 1400° C. Thus, the sintering of the particles of the compacted pellet is achieved.

It is important to highlight that this maximum temperature applied during step (3), or (f), to achieve the sintering of the compacted powder, prepared beforehand by the process according to the invention, is at least 100° C., or even at least 300° C., lower than that which is necessary to achieve the sintering of a powder which is compacted but prepared according to the processes of prior art. The process for manufacturing a pellet of an oxide of at least one metal according to the invention thus has an obvious advantage because of the further reduction in heat energy requirements, which is added to those previously mentioned, which are related to the process for preparing a powder of an oxide of at least one metal, such as the drastic limitation in the number of steps.

The invention relates, fifthly, to a pellet of an oxide of at least one metal, each metal having an oxidation number between (III) and (VI), obtained by the implementation of the manufacturing process as defined above, the advantageous characteristics of this process possibly being taken alone or in combination.

The invention relates, sixthly, to different uses of such a pellet of an oxide of at least one metal, each metal having an oxidation number between (III) and (VI).

According to the invention, this pellet of an oxide of at least one metal can be used as a nuclear fuel.

According to the invention, this pellet of an oxide of at least one metal can also be used as an ionic conductor, this ionic conductor possibly being in particular a solid electrolyte for a solid oxide fuel cell (SOFC) or an oxygen measuring probe, as previously mentioned.

Further characteristics and advantages of the invention will be better appear upon reading the complementary description that follows and which relates to exemplary synthesis of metal oxides according to the invention, wherein such oxides can be single or mixed oxides, being hydrated and/or anhydrous.

Of course, these examples are only given by way of illustration of the object of the invention and are in no way to be construed as a limitation of this object in any way.

DETAILED DISCLOSURE OF PARTICULAR EMBODIMENTS

Example 1: Synthesis of Hydrated and Anhydrous Uranium(IV) Oxides

Preparation of an Aqueous Solution Comprising a Uranium (IV) Chloride

For the synthesis of the hydrated uranium(IV) oxide and then of the anhydrous uranium(IV) oxide, an aqueous solution comprising a uranium chloride has been prepared from metal uranium $U^0$.

To this end, metal uranium chips have been washed with hydrochloric acid with a molar concentration of 2 mol/l in order to remove the oxide layer covering them. The washed uranium $U^0$ chips have then been introduced into a hydrochloric acid solution with a molar concentration of 6 mol/l. This introduction has been made by introducing, one by one, said chips in order to avoid a reaction runaway.

After dissolving said chips into the hydrochloric acid solution, an aqueous solution comprising uranium(IV) chloride is obtained the fines of which are separated by centrifugation.

This aqueous solution comprising uranium(IV) chloride thus obtained is titrated by a dosage metric assay as well as by Inductively coupled plasma-atomic emission spectrometry (ICP-AES).

Synthesis of the Hydrated Uranium(IV) Oxide

The synthesis of the hydrated uranium(IV) oxide has been made by adding, to the aqueous solution of uranium(IV) chloride as prepared above, ammonium hydroxide with a molar content of 400% with respect to the molar content of uranium chloride in the aqueous solution. This addition has been made at room temperature and under stirring, at a speed of 500 rpm. The stirring has been maintained for a period of time of one hour.

At the end of this hour, a precipitate has been obtained. After filtering the precipitate, the analysis by ICP-AES of the filtrate shows a quantitative uranium precipitation with a precipitation yield equal to or higher than 99.9%.

After washing several times with deionized water, and then with ethanol, enabling any residual acid trace to be removed, the precipitate is separated from the liquid phase by centrifugation at a speed of 4000 rpm. The precipitate thus obtained is divided into two fractions.

The first fraction of the precipitate is then subjected to an air drying, for 24 hours, at room temperature and under atmospheric pressure. The powder as obtained after this air drying step has been analysed.

The specific surface area as measured according to the BET method, by nitrogen adsorption at the boiling temperature of liquid nitrogen (−196° C.), is in the order of 30 m²/g.

Figure 1:
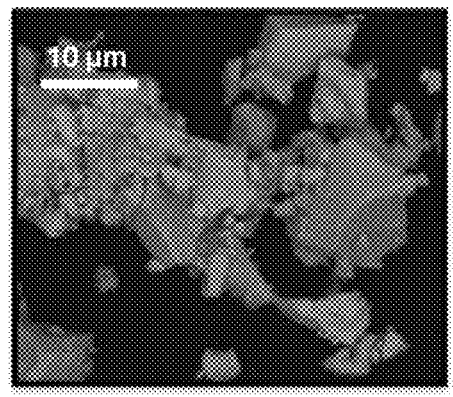
FIG. 1 corresponds to a picture made by means of a scanning electron microscope (SEM) of the reference powder of example 1.

A morphological study of this powder has also been made by scanning electron microscopy (SEM). The corresponding picture, which is illustrated in FIG. 1, shows that the particles forming the powder are strongly agglomerated.

The second fraction of the precipitate is in turn introduced in a flask with ethanol.

In order to allow for the quick evaporation at a low temperature of the ethanol present in the precipitate, the flask is placed under a dynamic vacuum lower than 100 Pa (1 mbar), by means of a vacuum manifold. The precipitate is simultaneously stirred at a speed of 500 rpm, at a temperature of 40° C.

At the end of this ethanol evaporation step, a powder is obtained. The stirring of this powder is maintained for 5 minutes and then the vacuum is released by introducing dinitrogen $N_2$, into the flask, by means of the vacuum manifold, to avoid the oxidation of uranium(IV).

This powder as obtained after the vacuum drying step of the second fraction of the precipitate has been analysed.

The specific surface area as measured according to the BET method, by nitrogen adsorption at the boiling temperature of liquid nitrogen (−196° C.), is in the order of 150 $m^2/g$. This value, which corresponds to a large specific surface area, reflects a strong reactivity of the powder thus obtained, which reactivity is remarkably higher than the powder obtained by air drying.

Figure 2A:
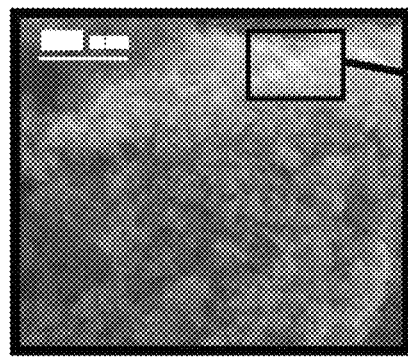
FIGS. 2A and 2B correspond to pictures made by means of a scanning electron microscope (FIG. 2A) and a transmission electron microscope (FIG. 2B) respectively of the powder according to the invention of example 1.
Figure 2B:
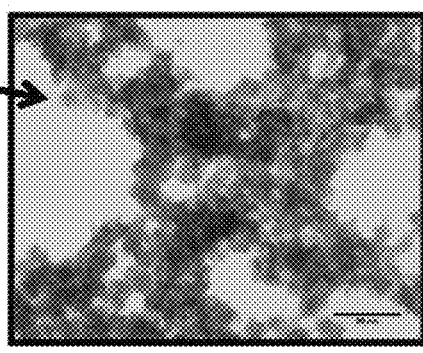

A morphological study of this vacuum dried powder has also been made by scanning electron microscopy (SEM). The corresponding picture, which is illustrated in FIG. 2A, shows that this powder does not agglomerate and that it is comprised of nanosize particles. This observation is, on the other hand, confirmed by the picture made by transmission electron microscopy (TEM) and which is illustrated in FIG. 2B. Indeed, this picture of FIG. 2B highlights the presence of particles in the order of about ten nanometers.

At the end of this vacuum drying step made on the second fraction of the precipitate, a powder is obtained which does not form aggregates and which has a strongly increased reactivity with respect to that of the powder which is obtained when the air drying of the same precipitate is conducted.

Figure 3:
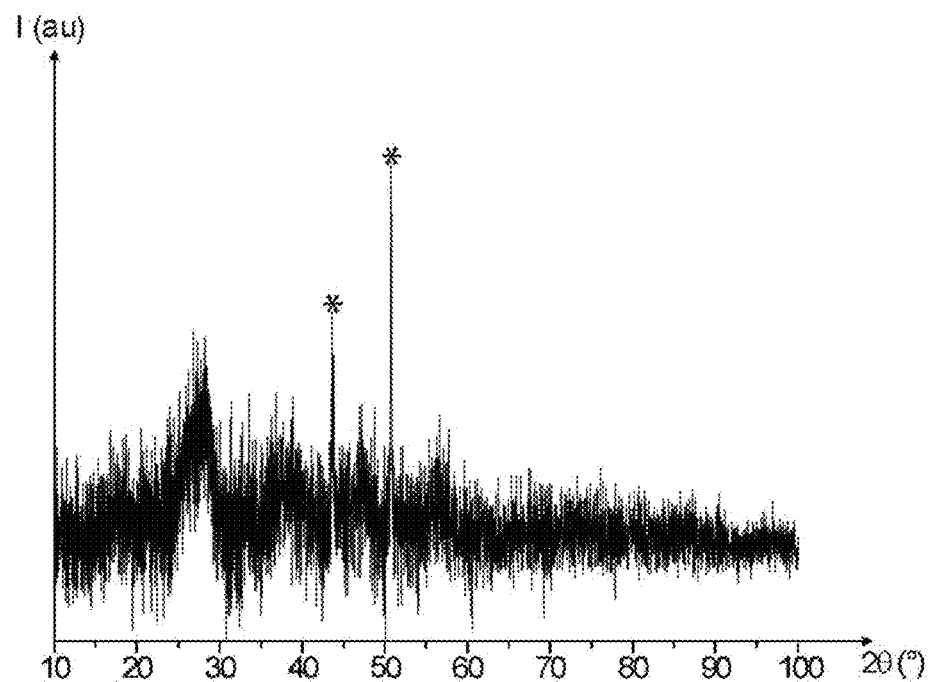
FIG. 3 represents an X ray diffraction pattern, obtained by the X ray diffraction (XRD) analysis technique, reflecting the change in the intensity of diffracted X rays as detected (noted I and expressed in arbitrary unit au) as a function of the diffraction angle two-theta of the beam of said X rays (noted 2θ and expressed in °), for the powder according to the invention of example 1.

In order to determine the structure of the particles of this vacuum dried powder, an X ray diffraction (XRD) analysis has been made. The corresponding X ray diffraction pattern is illustrated in FIG. 3, given that the two largest peaks located at the values of angle 2θ of about 43.5° and 50.5°, and marked by a star (*), correspond to the intensity of the X ray diffracted by the support of the powder sample.

It is observed that the X ray diffraction pattern thus obtained suggests a fluorite-type face-centered cubic crystallographic structure, of a space group Fm-3m, which is characteristic of actinides dioxides. On the other hand, this X ray diffraction pattern also emphasizes a low crystallinity exhibited by the particles forming the powder.

A complementary analysis by Raman spectrometry emphasizes the absence of the characteristic vibrational band of the OH groups and confirms the presence of a hydrated oxide.

These analyses by XRD and Raman spectroscopy enable reaction phenomena which occur upon reacting uranium chloride with ammonium hydroxide to be explained.

Indeed, in contact with ammonium hydroxide, cations $U^{4+}$ present in the uranium chloride aqueous solution precipitate as a uranium(IV) hydroxide, in accordance with the following chemical reaction (1):

(1)

But, this uranium(IV) hydroxide $U(OH)_4$ precipitate is a very reactive compound which spontaneously changes to the formation of the hydrated uranium(IV) oxide, according to the following chemical reaction (2):

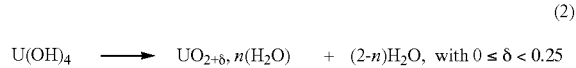

(2)

Heat Treatments of the Hydrated Uranium(IV) Oxide

In a first heat treatment, the follow-up of the change in the crystallinity of the powder of hydrated uranium(IV) oxide as a function of temperature has been conducted. This heat treatment has been made in situ, under inert atmosphere, in the presence of dinitrogen, by applying a temperature gradient increasing from 30° C. to 1100° C.

Figure 4:
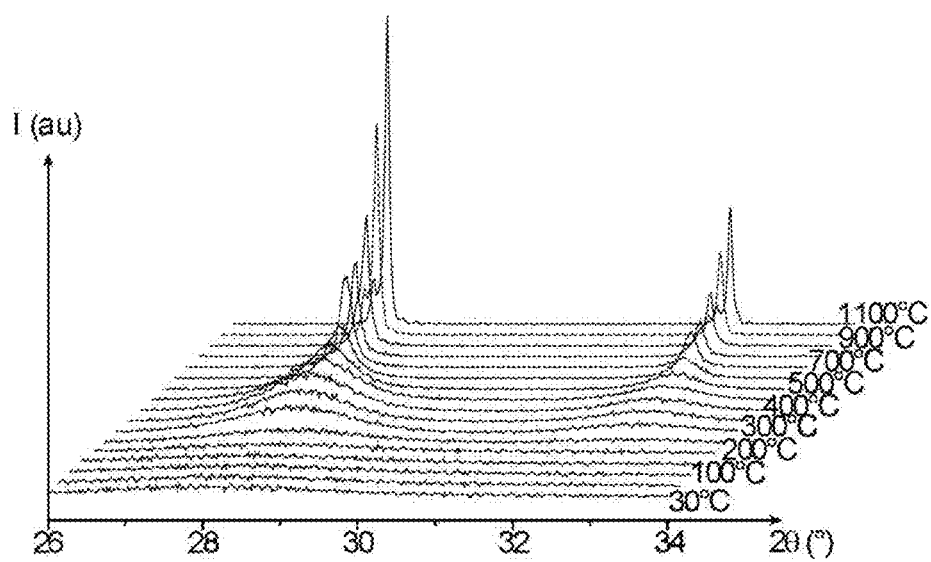
FIG. 4 represents the temperature X ray diffraction patterns as obtained between 30 and 1100° C. by the X ray diffraction (XRD) analysis technique, reflecting the change in the intensity of the diffracted X rays as detected (noted I and expressed in arbitrary unit au) as a function of the diffraction angle two-theta of the beam of said X rays (noted 2θ and expressed in °), for the powder according to the invention of example 1.

The X ray diffraction patterns thus obtained and illustrated in FIG. 4 show that the fluorite-type face-centered cubic crystallographic structure is preserved during this first heat treatment, and that the crystallinity of the powder is remarkably improved from an applied temperature of 600° C.

During a second heat treatment, the full dehydration of the powder of hydrated uranium(IV) oxide has been conducted, under inert atmosphere, more precisely under argon.

This dehydration has been followed by a thermogravimetric analysis in order to observe the change in the weight of the powder sample of hydrated uranium(IV) oxide as a function of the temperature applied. The corresponding curve is illustrated in FIG. 5.

Figure 5:
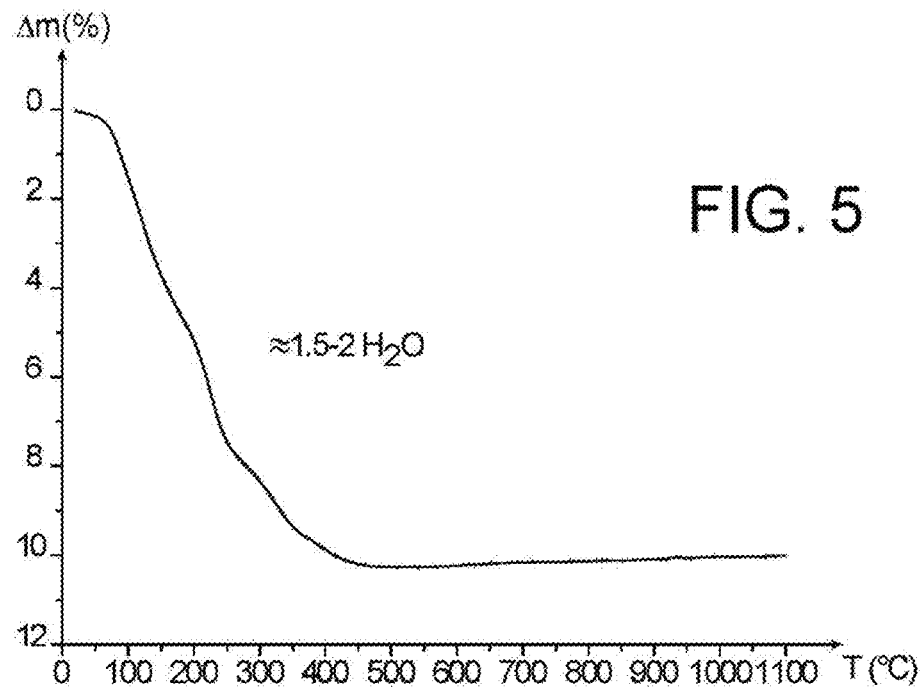
FIG. 5 illustrates the curve reflecting the change in the relative weight loss (noted Δm and expressed in %) for the sample of powder of hydrated uranium(IV) oxide according to the invention of example 1, as a function of the temperature applied (noted T and expressed in ° C.).

By referring to this FIG. 5, it is observed that the dehydration of the powder occurs in a single step which is completed at a temperature in the order of 450° C. From this temperature value, the maximum value of relative weight loss is reached. This value, which is in the order of 10%, corresponds to the full dehydration of the hydrated uranium (IV) oxide into anhydrous uranium(IV) oxide. This relative weight loss observed on the curve of FIG. 5 corresponds to a loss of 1.5 to 2 water molecules.

Compacting the Hydrated Uranium(IV) Oxide

The powder of hydrated uranium(IV) oxide as obtained after the vacuum drying step is compacted by uniaxial pressing at a pressure of 500 MPa. This compacting, also called "pelleting", made it possible to obtain a green pellet which has a density between 40% and 45%.

Densification of the Hydrated Uranium(IV) Oxide

A follow-up of the linear shrinkage of this compacted pellet has been performed by dilatometry as a function of temperature. The corresponding curve obtained is illustrated in FIG. 6.

Figure 6:
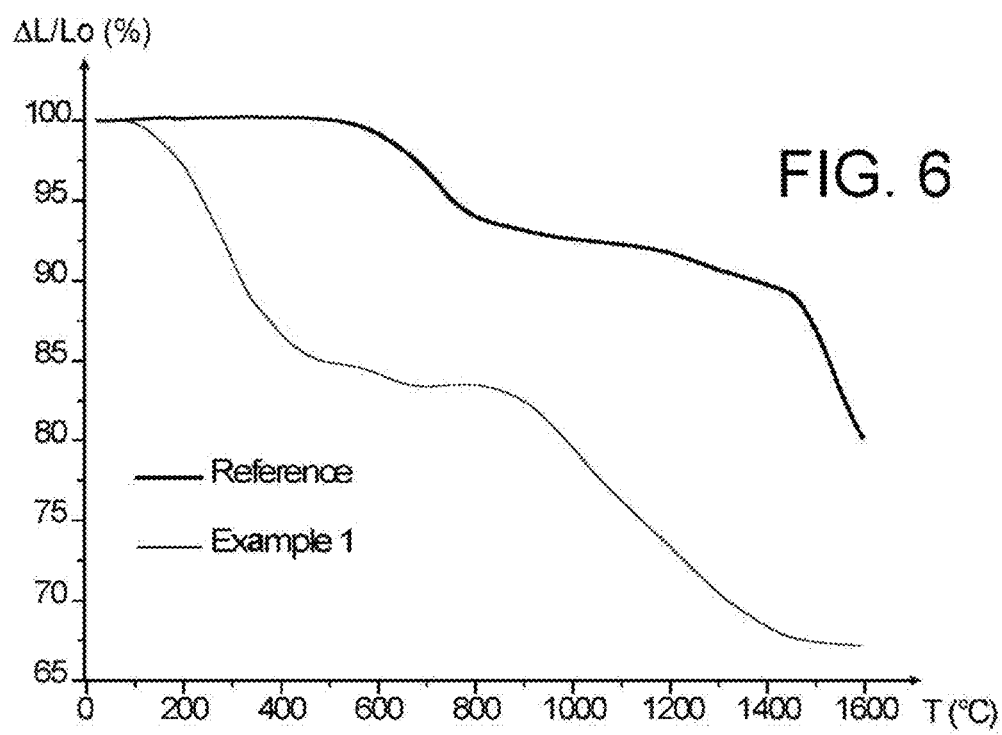
FIG. 6 illustrates the curve reflecting the change in the relative linear shrinkage (noted $\Delta L/L_0$ and expressed in %) of a reference pellet as well as of a pellet obtained after compacting the powder of hydrated uranium(IV) oxide according to the invention of example 1 as a function of the temperature applied (noted T and expressed in ° C.).

This curve of FIG. 6 has two parts, a first part extending from room temperature to a temperature of about 800° C., which corresponds to the temperature interval in which the dehydration of hydrated uranium(IV) oxide into anhydrous uranium(IV) oxide occurs, as well as a second part, extending from about 800° C. to about 1600° C., which corresponds to the temperature interval in which the sintering of the anhydrous uranium(IV) oxide particles forming the pellet occurs.

By way of comparison, in the same FIG. 6, is reported the linear shrinkage curve of the reference pellet compacted under the same conditions as the previous pellet, but performed from a powder prepared by the process described in the publication by N. Hingant et al. ("*Preparation, sintering and leaching of optimized uranium thorium dioxides*", Journal of Nuclear materials, 385 (2009), 400-406), hereinafter referred as [5].

It is set forth that the powder obtained according to the process of document [5] has particles of about 1 μm, given that these particles as obtained at the end of this process are agglomerated as square plates of about 5 μm to 10 μm side. This agglomeration phenomenon occurs both before and after drying, regardless of whether the drying step is made in the air, or even according to the characteristics of steps (c) and (d) of the preparing process according to the invention.

Therefore, it is observed that the maximum linear shrinkage speed is achieved at a temperature equal to or higher than 1600° C. with the reference pellet whereas it is reached at a temperature in the order of 1200° C. with a pellet obtained according to the process according to the invention, that is with a gain in the order of 400° C.

Geometrical measurements made it possible to characterize the pellet obtained in accordance with the process according to the invention, at the end of the dilatometry analysis. Such geometrical measurements indicate that the material obtained is a dense material, having a density of 95%.

Figure 7:
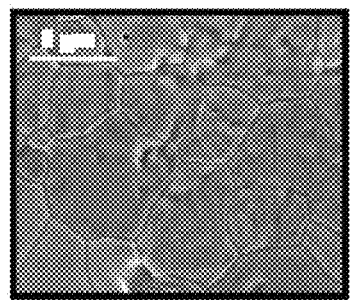
FIG. 7 corresponds to a picture taken by means of a scanning electron microscope of the pellet according to the invention of example 1, after sintering.

This observation is confirmed by the micrographic picture (SEM) of FIG. 7 of this same pellet obtained after heat treatment. This picture clearly emphasizes that the material obtained after sintering of the pellet of anhydrous uranium oxide is particularly dense.

Example 2: Synthesis of the Hydrated Cerium(IV) Oxide

Preparation of an Aqueous Solution Comprising a Cerium (IV) Sulphate

For the synthesis of the hydrated cerium(IV) oxide, an aqueous solution comprising cerium(IV) sulphate has been prepared by dissolving hydrated cerium sulphate in deionized water and then diluting, still in deionized water, to reach the desired concentration.

In order to minimize mistakes related to the hygroscopic character of cerium(IV) sulphate, this aqueous solution comprising cerium(IV) sulphate is titrated by inductively coupled plasma-atomic emission spectrometry (ICP-AES).
Synthesis of the Hydrated Cerium(IV) Oxide The synthesis of the hydrated cerium(IV) oxide has been made by adding, to the cerium sulphate aqueous solution as prepared above, ammonium hydroxide with a molar content of 400% with respect to the molar content of cerium(IV) sulphate in the aqueous solution. This addition has been made at room temperature and under stirring, at a speed of 500 rpm. The stirring has been maintained for a period of time of one hour.

At the end of this hour, a precipitate has been obtained. After filtering the precipitate, the analysis by ICP-AES of the filtrate shows a quantitative precipitation of cerium with a precipitation yield equal to or higher than 99.9%.

After washing several times with deionized water, and then with ethanol, enabling any residual acid trace to be removed, the precipitate is separated from the liquid phase by centrifugation at a speed of 4000 rpm.

The precipitate thus obtained is then introduced in a flask with ethanol. The flask comprising the precipitate and ethanol is then placed under a dynamic vacuum lower than 100 Pa (1 mbar) by means of a vacuum manifold. The precipitate is stirred at a speed of 500 rpm, at a temperature of 40° C. to enable ethanol to be evaporated.

At the end of this ethanol evaporation step, a powder is obtained. The stirring of this powder is maintained for 5 minutes and then the vacuum is released.

This powder as obtained after the vacuum drying step of the precipitate has been analysed.

The specific surface area as measured according to the BET method, by nitrogen adsorption at the boiling temperature of liquid nitrogen (−196° C.), is in the order of 120 m$^2$/g, which value corresponds to a significant specific surface area and which reflects a strong reactivity of the powder thus obtained.

Figure 8:
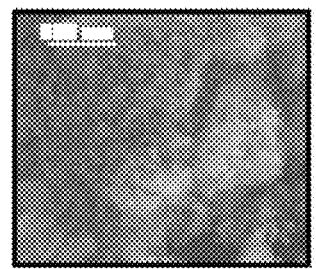
FIG. 8 corresponds to a picture taken by means of a scanning electron microscope (SEM) of the powder according to the invention of example 2.

A morphological study of this powder has also been made by scanning electron microscopy (SEM). The corresponding picture, which is illustrated in FIG. 8, shows that this powder does not agglomerate and that it is comprised of nanoscale particles.

Figure 9:
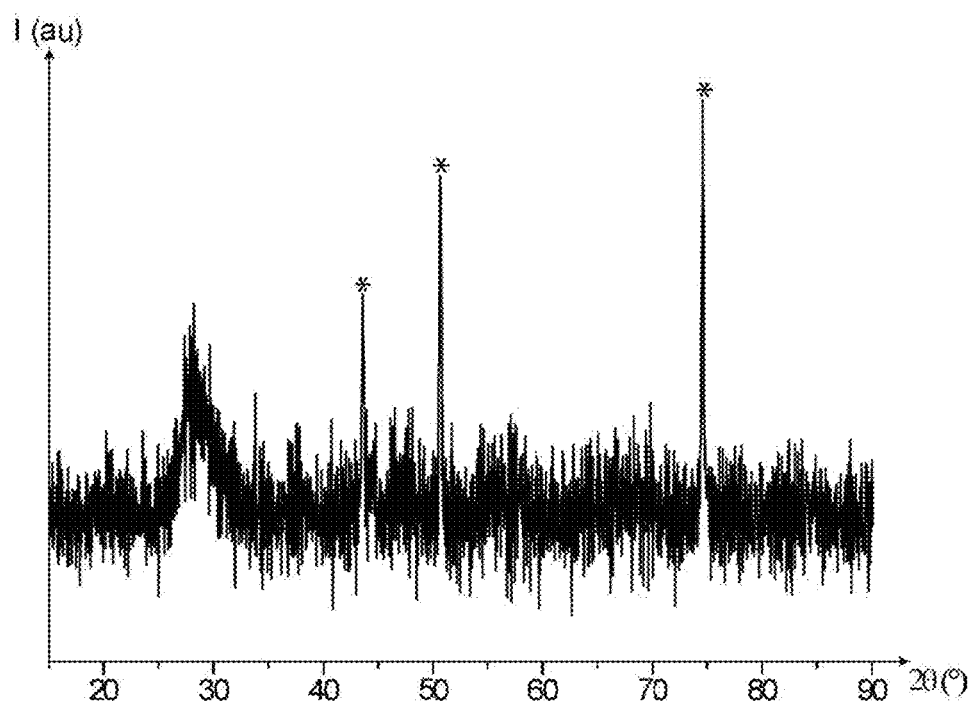
FIG. 9 represents an X ray diffraction pattern, obtained by the X ray diffraction (XRD) analysis technique, reflecting the change in the intensity of the diffracted X rays as detected (noted I and expressed in arbitrary unit au) as a function of the diffraction angle two-theta of the beam of said X rays (noted 2θ and expressed in °), for the powder according to the invention of example 2.

In order to determine the structure of the particles of the powder obtained from the precipitate, an X ray diffraction (XRD) analysis has been performed. The corresponding X ray diffraction pattern is illustrated in FIG. 9, given that the three largest peaks located at the 2θ angle values of about 43°, 50° and 75°, and marked with a star (*), correspond to the intensity of X rays diffracted by the powder sample support.

It is observed that the X ray diffraction pattern thus obtained reveals a fluorite-type face-centered cubic crystallographic structure, of a space group Fm-3m, which is characteristic of the cerium dioxide. On the other hand, this X ray diffraction pattern also emphasizes a low crystallinity exhibited by the particles forming the powder.

A complementary analysis by Raman spectrometry emphasizes the absence of the characteristic vibrational band of the OH groups and confirms the presence of a hydrated oxide.

These analyses by XRD and Raman spectrometry enable reaction phenomena which occur upon reacting the cerium sulphate with ammonium hydroxide to be explained.

Indeed, in contact with ammonium hydroxide, the cations Ce$^{4+}$ present in the cerium(IV) sulphate aqueous solution precipitate as a cerium(IV) hydroxide, in accordance with the following chemical reaction (3):

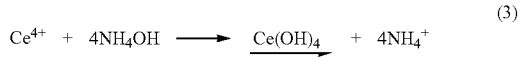

$$Ce^{4+} + 4NH_4OH \longrightarrow Ce(OH)_4 + 4NH_4^+ \quad (3)$$

But, this cerium(IV) hydroxide Ce(OH)$_4$ precipitate is a very reactive compound which spontaneously changes to the formation of a hydrated cerium(IV) oxide, according to the following chemical reaction (4):

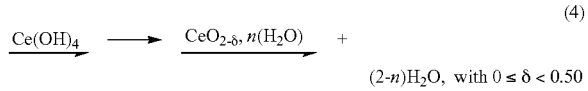

$$Ce(OH)_4 \longrightarrow CeO_{2-\delta}, n(H_2O) + (2-n)H_2O, \text{ with } 0 \leq \delta < 0.50 \quad (4)$$

Example 3: Synthesis of the Hydrated Thorium(IV) Oxide

Preparation of an Aqueous Solution Comprising Thorium (IV) Nitrate

For the synthesis of the hydrated thorium(IV) oxide, an aqueous solution comprising thorium(IV) nitrate has been prepared by dissolving hydrated thorium nitrate in hydrochloric acid at a molar concentration of 6 mol/l.

In order to minimize mistakes related to the hygroscopic character of thorium(IV) nitrate, this aqueous solution comprising thorium(IV) nitrate is titrated by inductively coupled plasma-atomic emission spectrometry (ICP-AES).

Synthesis of the Hydrated Thorium(IV) Oxide

The synthesis of the hydrated thorium(IV) oxide has been made by adding, to the thorium nitrate aqueous solution as prepared above, ammonium hydroxide at a molar content of 400% with respect to the molar content of thorium(IV) nitrate in the aqueous solution. This addition has been made at room temperature and under stirring, at a speed of 500 rpm. The stirring has been maintained for a period of time of one hour.

At the end of this hour, a precipitate has been obtained. After filtering the precipitate, the analysis by ICP-AES of the filtrate shows a quantitative precipitation of thorium with a precipitation yield equal to or higher than 99.9%.

After washing several times with deionized water, and then with ethanol, enabling any residual acid trace to be removed, the precipitate is separated from the liquid phase by centrifugation at a speed of 4000 rpm.

The precipitate thus obtained is then introduced in a flask with ethanol. The flask comprising the precipitate and ethanol is then placed under a dynamic vacuum lower than 100 Pa (1 mbar) by means of a vacuum manifold. The precipitate is stirred at a speed of 500 rpm, at a temperature of 40° C. to enable ethanol to be evaporated.

At the end of this ethanol evaporation step, a powder is obtained. The stirring of this powder is maintained for 5 minutes and then the vacuum is released.

This powder as obtained after the vacuum drying step of the precipitate has been analysed.

The specific surface area as measured according to the BET method, by nitrogen adsorption at the boiling temperature of liquid nitrogen (−196° C.) is higher than 150 m²/g, which value corresponds to a very significant specific surface area and which reflects a very strong reactivity of the powder thus obtained.

As in the case of the powders of examples 1 and 2 as obtained by the process according to the invention, complementary analyses show that the powder obtained is hydrated thorium(IV) oxide.

Indeed, in contact with ammonium hydroxide, cations $Th^{4+}$ present in the thorium(IV) nitrate aqueous solution precipitate as thorium(IV) hydroxide, in accordance with the following chemical reaction (5):

(5)

But, this precipitate of thorium(IV) hydroxide $Th(OH)_4$ is a very reactive compound which spontaneously changes to the formation of a hydrated thorium(IV) oxide, according to the following chemical reaction (6):

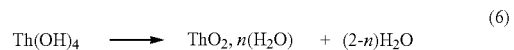

(6)

Example 4: Synthesis of Hydrated and Anhydrous Uranium(IV) and Cerium(IV) Mixed Oxides Preparation of the Aqueous Solutions An aqueous solution comprising uranium(IV) chloride has been prepared by dissolving metal uranium $U^0$ in hydrochloric acid (6M), as in example 1.

An aqueous solution comprising cerium(IV) sulphate has been prepared by dissolving hydrated cerium sulphate in deionized water and then diluting, still in deionized water, to reach the desired concentration, as in example 2.

As previously, each of these aqueous solutions has been titrated by a dosage colour assay and by ICP-AES.

Synthesis of Hydrated Uranium(IV) and Cerium(IV) Mixed Oxides

Three mixtures, noted A, B and C, have been made from the aqueous solutions as prepared in the previous step, in the stoichiometries of the elements cerium and uranium, respectively noted x and (1−x), as reported in table 1 below.

TABLE 1

| Mixtures | A | B | C |
| --- | --- | --- | --- |
| x, [Ce⁴⁺] | 0.1 | 0.2 | 0.45 |
| (1 − x), [U⁴⁺] | 0.9 | 0.8 | 0.55 |

The synthesis of the hydrated uranium(IV) and cerium (IV) mixed oxides has been made by adding, to each of the mixtures A to C as prepared above, ammonium hydroxide at a molar content of 400% with respect to the sum of the molar contents of uranium(IV) chloride and of cerium(IV) sulphate present in the mixtures A to C. In the three tests, the addition of ammonium hydroxide has been made at room temperature and under stirring, at a speed of 500 rpm. The stirring has been maintained for a period of time of one hour.

At the end of this hour, precipitates have been obtained. After filtering these precipitates, the analyses by ICP-AES of each of the filtrates show a quantitative precipitation of uranium and of cerium with precipitation yields equal to or higher than 99.9%.

After washing several times with deionized water, and then with ethanol, enabling any residual acid trace to be removed, each of the precipitates is separated from the liquid phase by centrifugation at a speed of 4000 rpm.

Each of the precipitates thus separated is then contacted with a solvent which is either ethanol or water.

To this end, each precipitate thus obtained is introduced in a flask with the solvent considered. The flask comprising the precipitate and the solvent is then placed under a dynamic vacuum lower than 100 Pa (1 mbar) by means of a vacuum manifold. The precipitate is stirred at a speed of 500 rpm, at a temperature of 40° C. to enable solvent to be evaporated.

At the end of this solvent evaporation step, a powder is obtained. The stirring of this powder is maintained for 5 minutes and then the vacuum is released by introducing nitrogen $N_2$, into the flask, by means of the vacuum manifold, to avoid oxidation of uranium(IV).

The powders as obtained after the vacuum drying step of each of the precipitates have been analysed.

The specific surface areas as measured according to the BET method, by nitrogen adsorption at the boiling temperature of liquid nitrogen (−196° C.), for each of the powders, are located in an interval of values between 100 m²/g and 150 m²/g in the case where the solvent, with which each of the precipitates has been contacted, is ethanol. Such values, which characterize a large specific surface area, reflect a strong reactivity of the powders in accordance with the invention, obtained from the mixtures A to C.

But, it is observed that, in the case where water has been used as a solvent, these same values of specific surface areas are lower than the previous ones since they are located in an interval between 10 m²/g and 30 m²/g.

Figures 10A, 10B, 10C:
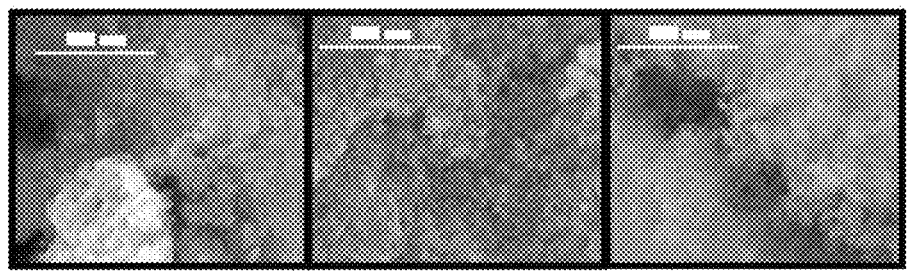
FIGS. 10A, 10B and 10C correspond to the pictures taken by means of a scanning electron microscope (SEM) of the powders according to the invention obtained from the mixtures A, B and C respectively, and in the presence of ethanol as a solvent, of example 4.

A morphological study of the three powders according to the invention, obtained after contacting with ethanol as a solvent, has also been made by scanning electron microscopy (SEM). The corresponding pictures, which are illustrated in FIGS. 10A, 10B and 10C, show that the three powders do not agglomerate and that they are comprised of nanosize particles.

Figure 10D:
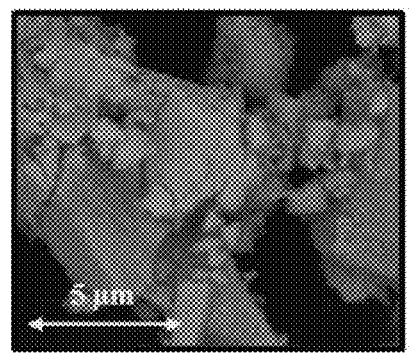
FIG. 10D corresponds to the picture taken by means of the scanning electron microscope (SEM) of the comparative powder, obtained from the mixture A, and in the presence of water as a solvent, of example 4.

By way of comparison, the picture of FIG. 10D of the comparative powder obtained from the mixture A, but after contacting with water as a solvent, shows an agglomerated powder, comprised of micronize agglomerates.

In order to determine the structure of the particles of the three powders in accordance with the invention, analyses by X ray diffraction (XRD) have been made. The corresponding X ray diffraction patterns are illustrated in FIG. 11.

Figure 11:
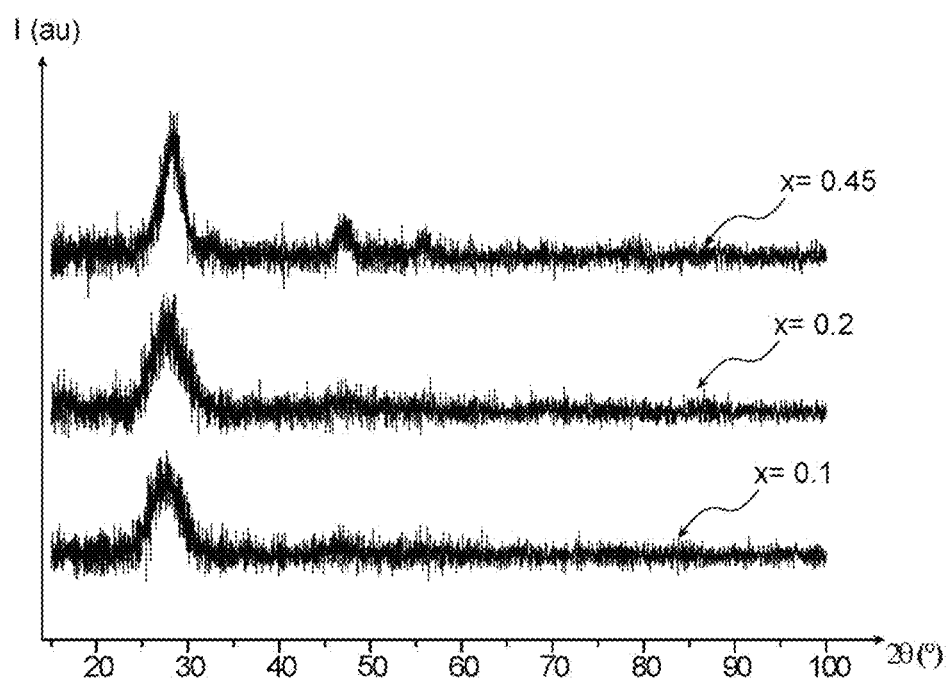
FIG. 11 represents the X ray diffraction patterns, obtained by the X ray diffraction (XRD) analysis technique, reflecting the change in the intensity of the diffracted X rays as detected (noted I and expressed in arbitrary unit au) as a function of the diffraction angle two-theta of the beam of said X rays (noted 2θ and expressed in °), for the powders obtained from the mixtures A, B and C respectively, of example 4.

It is observed that the X ray diffraction patterns of FIG. 11 all reveal the presence of a solid having a fluorite-type face-centered cubic crystallographic structure, of a space group Fm-3m, which is characteristic of actinides mixed dioxides. On the other hand, these X ray diffraction patterns also emphasize a low crystallinity exhibited by the particles forming these three powders.

Complementary analyses by Raman spectrometry emphasize the absence of the characteristic vibrational band of the OH groups and confirm the presence of a hydrated mixed oxide.

These analyses by XRD and Raman spectrometry enable reaction phenomena which occur upon reacting uranium(IV) chloride and cerium(IV) sulphate with ammonium hydroxide to be explained.

Indeed, in contact with ammonium hydroxide, cations $U^{4+}$ and $Ce^{4+}$ present in the mixtures A to C precipitate as a uranium(IV) and cerium(IV) mixed hydroxide, in accordance with the following chemical reaction (7):

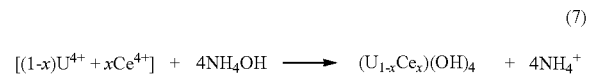

(7)

But, this uranium(IV) and cerium(IV) mixed hydroxide precipitate is a very reactive compound which spontaneously changes to the formation of a hydrated uranium(IV) and cerium(IV) mixed oxide, according to the following chemical reaction (8):

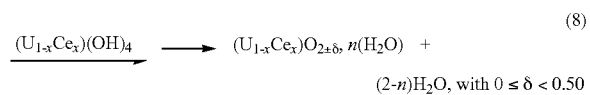

(8)

Compacting Hydrated Mixed Uranium(IV) and Cerium(IV) Oxides

The powders of hydrated uranium (IV) and cerium (IV) mixed oxides in accordance with the invention, as obtained from the mixtures A to C, are compacted by uniaxial pressing at a pressure of 500 M Pa. The green pellets thus obtained all exhibit a density between 40% and 45%.

Sintering the Hydrated Uranium(IV) and Cerium(IV) Mixed Oxides

A follow-up of the linear shrinkage of the compacted pellets has been performed by dilatometry as a function of temperature. The three corresponding curves obtained are illustrated in FIG. 12.

Figure 12:
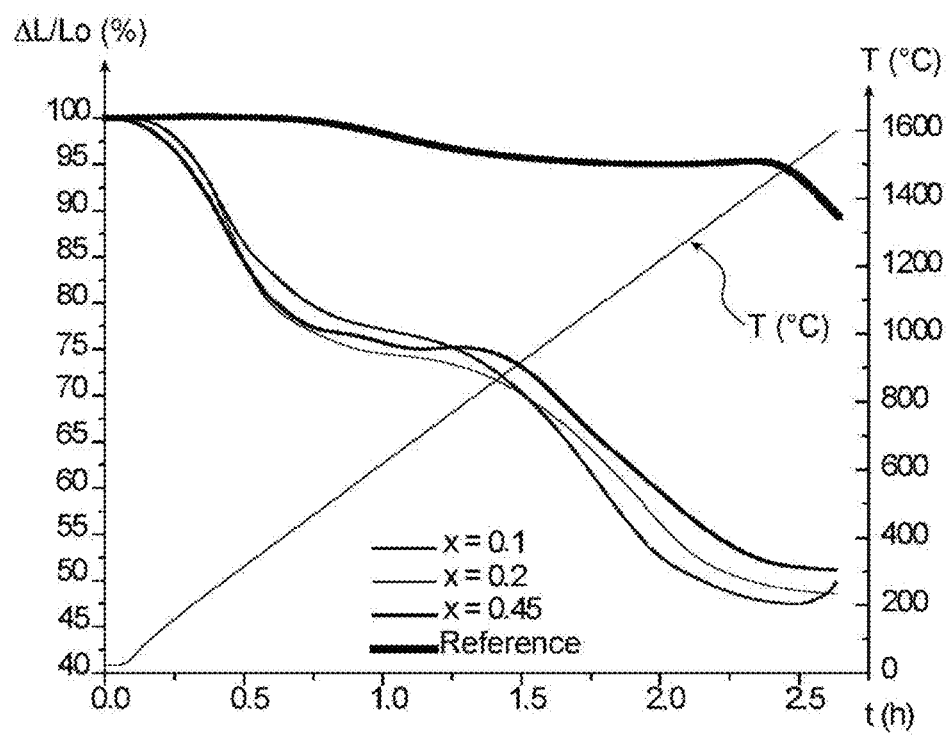
FIG. 12 illustrates the curves reflecting the change in the relative linear shrinkage (noted $\Delta L/L_0$ and expressed in %) of a reference pellet as well as of each of the pellets obtained after compacting the powders of uranium(IV) and cerium (IV) mixed oxides according to the invention of example 4, as a function of the temperature applied (noted T and expressed in ° C.) and time (noted t and expressed in hours).

These curves of FIG. 12 have two parts, a first part extending from room temperature to a temperature of about 900° C., which corresponds to the temperature interval in which the dehydration of hydrated uranium(IV) and cerium (IV) mixed oxides in anhydrous uranium(IV) and cerium (IV) mixed oxides occurs, as well as a second part, extending to about 900° C. to about 1600° C., which corresponds to the temperature interval in which the sintering of the particles of anhydrous uranium(IV) and cerium(IV) mixed oxides forming each of the pellets occurs.

By way of comparison, in the same FIG. 12, is reported the curve of linear shrinkage of a reference pellet compacted according to the same conditions as the pellets of uranium (IV) and cerium(IV) mixed oxides, but made from a powder prepared by the process described in document [5].

It is thus observed that the maximum speed of linear shrinkage is achieved at a temperature of about 1600° C. with the reference pellet whereas it is reached at a temperature in the order of 1100° C. to 1200° C. with a pellet obtained according to the process of the invention, that is with a gain in the order of 400° C. to 500° C.

Geometric measurements enable the pellet obtained to be characterized, from the mixture A (x=0.1), in accordance with the process according to the invention, at the end of the dilatometry analysis. Such geometrical measurements indicate that the material obtained is a dense material, having a density of 95%.

Figure 13:
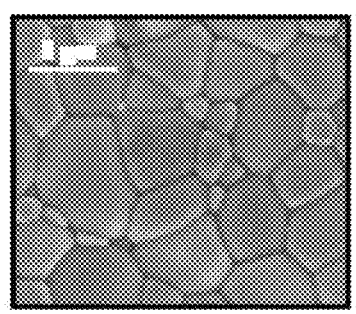
FIG. 13 corresponds to a picture taken by means of a scanning electron microscope of the pellet according to the invention of example 4 and obtained from the mixture A (x=0.1), after sintering.

This observation is confirmed by the micrographic picture (SEM) of FIG. 13 of this same pellet obtained after heat treatment. This picture clearly emphasizes that the material obtained after sintering of the pellet of anhydrous uranium (IV) and cerium(IV) mixed oxide (with x=0.1) is particularly dense.

Example 5: Synthesis of a Hydrated Cerium(IV) and Gadolinium(III) Mixed Oxide

Preparation of the Aqueous Solutions

An aqueous solution comprising cerium(III) chloride has been prepared by dissolving hydrated cerium(III) chloride in deionized water and then diluting, still in deionized water, to reach the desired concentration.

An aqueous solution comprising gadolinium(III) chloride has been prepared by dissolving hydrated gadolinium(III) chloride in deionized water and then diluting, still in deionized water, to reach the desired concentration.

As previously, each of these aqueous solutions has been titrated by dosage colour assay and by ICP-AES.

Synthesis of a Hydrated Cerium(IV) and Gadolinium(III) Mixed Oxide

A mixture, noted D, has been made from the aqueous solutions as prepared in the previous step, with a molar proportion of 20% of gadolinium element, noted z, with z=0.2.

The synthesis of the hydrated cerium(IV) and gadolinium (III) mixed oxide has been made by adding, to the mixture D as prepared above, ammonium hydroxide with a molar content of 400% with respect to the sum of the molar contents of cerium(III) chloride and gadolinium(III) chloride present in the mixture D. This addition of ammonium hydroxide has been made at room temperature and under stirring, at a speed of 500 rpm. The stirring has been maintained for a period of time of one hour.

At the end of this hour, a precipitate has been obtained. After filtering the precipitate, the analysis by ICP-AES of the filtrate shows a quantitative precipitation of cerium and gadolinium with a precipitation yield equal to or higher than 99.9%.

After washing several times with deionized water, and then with ethanol, enabling any residual acid trace to be removed, the precipitate is separated from the liquid phase by centrifugation at a speed of 4000 rpm.

The precipitate thus obtained is introduced into a flask with ethanol. The flask comprising the precipitate and ethanol is then placed under dynamic vacuum lower than 100 Pa (1 mbar) by means of a vacuum manifold. The precipitate is stirred at a speed of 500 rpm, at a temperature of 40° C. to enable ethanol to be evaporated.

At the end of this ethanol evaporation step, a powder is obtained. The stirring of this powder is maintained for 5 minutes and then the vacuum is released.

The powder as obtained after the vacuum drying step of the precipitate has been analysed.

The specific surface area as measured according to the BET method, by nitrogen adsorption at the boiling temperature of liquid nitrogen (−196° C.), is located in a value interval between 100 m²/g and 130 m²/g. This value, which corresponds to a large specific surface area, reflects a strong activity of the powder thus obtained.

Figure 14:
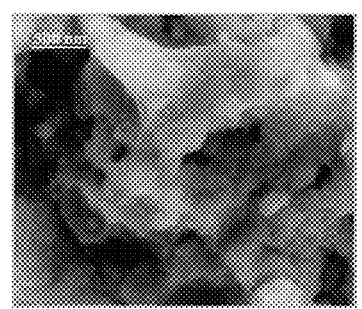
FIG. 14 corresponds to a picture taken by means of a scanning electron microscope (SEM) of the powder according to the invention of example 5.

A morphological study of the powder has also been made by scanning electron microscopy (SEM). The corresponding picture, illustrated in FIG. 14, shows that the powder does not agglomerate and that it is comprised of nanosize particles.

In order to determine the composition of the particles of this powder, an X ray diffraction (XRD) analysis has been made. The corresponding X ray diffraction pattern is illustrated in FIG. 15.

Figure 15:
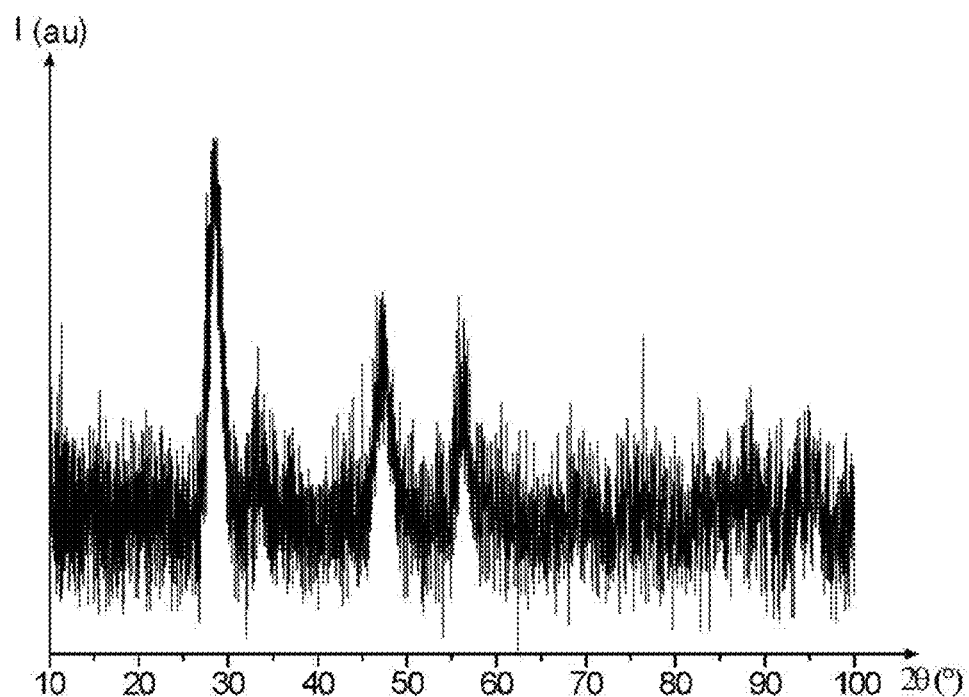
FIG. 15 represents the X ray diffraction pattern, obtained by the X ray diffraction (XRD) analysis technique, reflecting the change in the intensity of the diffracted X rays as detected (noted I and expressed in arbitrary unit au) as a function of the diffraction angle two-theta of the beam of said X rays (noted 2θ and expressed in °), for the powder according to the invention of example 5.

It is observed that the X ray diffraction pattern of FIG. 15 reveals the presence of a solid having a fluorite-type face-centered cubic crystallographic structure, of a space group Fm-3m, which is characteristic of cerium dioxide. On the other hand, this X ray diffraction pattern also emphasizes a low crystallinity exhibited by the particles forming the powder.

Complementary analyses by Raman spectrometry emphasize the absence of the characteristic vibration band of the OH groups and confirm the presence of a hydrated mixed oxide.

These analyses by DRX and Raman spectrometry enable reaction phenomena which occur upon reacting cerium(III) chloride and gadolinium(III) chloride with ammonium hydroxide to be explained.

Indeed, in contact with ammonium hydroxide, cations $Ce^{3+}$ and $Gd^{3+}$ present in the mixture D precipitate as a cerium(III) and gadolinium(III) mixed hydroxide, in accordance with the following chemical reaction (9):

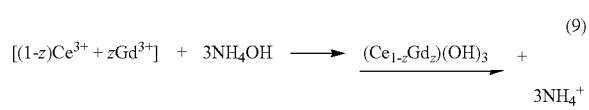

(9)

But, this precipitate of cerium(III) and gadolinium(III) mixed hydroxide is a very reactive compound which spontaneously changes to the formation of a hydrated cerium(IV) and gadolinium(III) mixed oxide, according to the following chemical reaction (10):

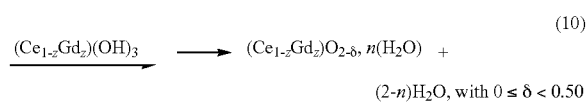

(10)

$(2-n)H_2O$, with $0 \leq \delta < 0.50$

Example 6: Synthesis of a Hydrated Thorium(IV) and Uranium(VI) Mixed Oxide

Preparation of the Aqueous Solutions

An aqueous solution comprising uranium(VI) nitrate has been prepared by dissolving uranium as $UO_4,4H_2O$ in nitric acid (6M).

An aqueous solution comprising thorium(IV) nitrate has been prepared by dissolving hydrated thorium nitrate in hydrochloric acid at a molar concentration of 6 mol/L.

In order to minimize mistakes relative to the hygroscopic character of thorium(IV) nitrate, this aqueous solution comprising thorium(IV) nitrate has been titrated by inductively coupled plasma-atomic emission spectrometry (ICP-AES).

Synthesis of a Hydrated Thorium(IV) and Uranium(VI) Mixed Oxide

A mixture, noted E, has been made from the aqueous solutions as prepared in the previous step, in the respective stoichiometries, of the elements thorium and uranium, of 0.8 and 0.2.

The synthesis of the hydrated thorium(IV) and uranium (VI) mixed oxide has been made by adding, to the mixture E as prepared above, ammonium hydroxide at a molar content of 400% with respect to the sum of the molar contents of thorium(IV) nitrate and uranium(VI) nitrate present in the mixture E. This addition of ammonium hydroxide has been made at room temperature and under stirring, at speed of 500 rpm. The stirring has been maintained for a period of time of one hour.

At the end of this hour, a precipitate has been obtained. After filtering this precipitate, the analyses by ICP-AES of the filtrate show a quantitative precipitation of uranium and thorium with a precipitation yield equal to or higher than 99.9%.

After washing several times with deionized water, and then with ethanol, enabling any residual acid trace to be removed, the precipitate is separated from the liquid phase by centrifugation at a speed of 4000 rpm.

The precipitate thus obtained is introduced into a flask with ethanol. The flask comprising the precipitate and ethanol is then placed under a dynamic vacuum lower than 100 Pa (1 mbar) by means of a vacuum manifold. The precipitate is stirred at a speed of 500 rpm, at a temperature of 40° C. to enable ethanol to be evaporated.

At the end of this ethanol evaporation step, a powder is obtained. The stirring of this powder is maintained for 5 minutes and then the vacuum is released by introducing dinitrogen $N_2$, into the flask, by means of the vacuum manifold.

The powder as obtained after the vacuum drying step of the precipitate has been analysed.

The specific surface area as measured according to the BET method, by nitrogen adsorption at the boiling temperature of liquid nitrogen (−196° C.), for this powder, is higher than 100 m²/g. Such a value, which characterizes a large specific surface area, reflects a strong reactivity of the powder obtained from the mixture E.

Figure 16:
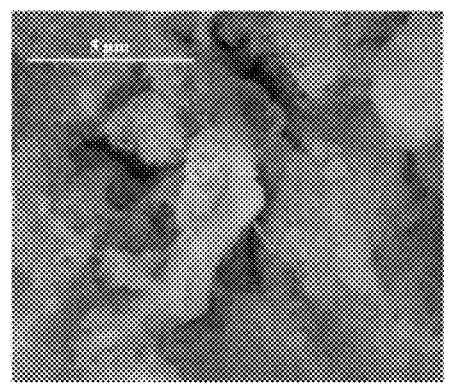
FIG. 16 corresponds to a picture taken by means of a scanning electron microscope (SEM) of the powder according to the invention of example 6.

A morphological study of the powder has also been made by scanning electron microscopy (SEM). The corresponding picture, which is illustrated in FIG. 16, shows that the powder does not agglomerate and that it is comprised of nanosize particles.

In order to determine the structure of the particles of this powder, an X ray diffraction (XRD) analysis has been made. The corresponding X ray diffraction pattern is illustrated in FIG. 17.

Figure 17:
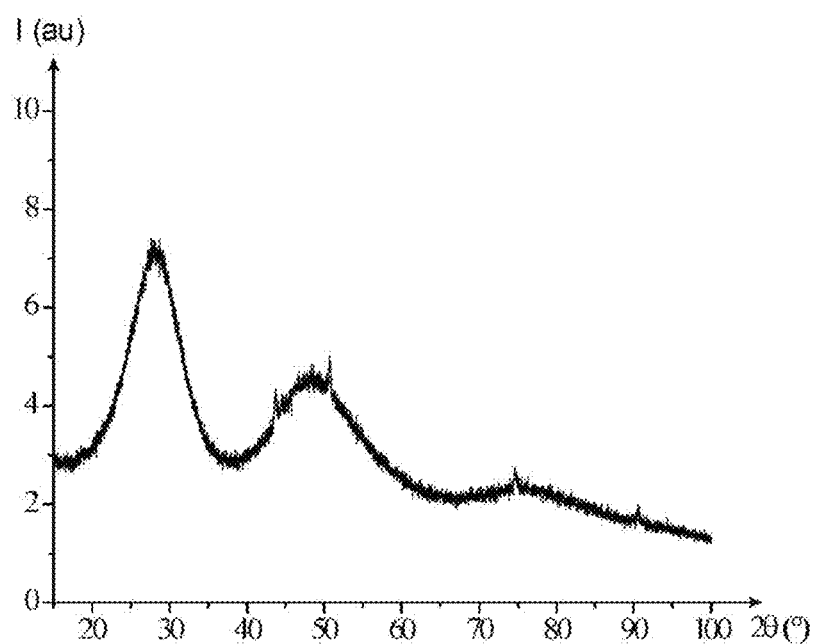
FIG. 17 represents the X ray diffraction pattern, obtained by the X ray diffraction (XRD) analysis technique, reflecting the change in the intensity of the diffracted X rays as detected (noted I and expressed in arbitrary unit au) as a function of the diffraction angle two-theta of the beam of said X rays (noted 2θ and expressed in °), for the powder according to the invention of example 6.

It is observed that the X ray diffraction pattern of FIG. 17 reveals the presence of a solid having a fluorite-type face-centered cubic crystallographic structure, of a space group Fm-3m, which is characteristic of the actinides mixed dioxides. On the other hand, this X ray diffraction pattern also emphasizes a low crystallinity exhibited by the particles forming this powder.

REFERENCE LIST

[1] GB 1,128,838
[2] U.S. Pat. No. 4,314,952
[3] U.S. Pat. No. 4,382,885
[4] U.S. Pat. No. 4,971,734
[5] N. Hingant et al., *Journal of Nuclear Materials*, 2009, 385, pages 400-406

The invention claimed is:

1. A process for preparing a powder of an oxide of at least one metal, each metal having an oxidation number between (III) and (VI), which process comprises successively and in this order:
   (a) reacting, with a compound comprising a hydroxide, an aqueous solution comprising, for each metal, at least one salt of the cation of said metal, leading to a precipitate of the hydrated oxide of said at least one metal,
   (b) separating the precipitate obtained,
   (c) contacting the separated precipitate with an organic protic polar solvent,
   (d) removing the organic protic polar solvent by vacuum drying the precipitate, leading to the powder of the hydrated oxide of said at least one metal, said powder being formed of particles the average diameter of which is equal to or lower than 1 µm.

2. The process according to claim 1, wherein the powder of the hydrated oxide of said at least one metal is formed of particles the average diameter of which is equal to or lower than 100 nm.

3. The process according to claim 1, wherein the powder of the hydrated oxide of said at least one metal has a specific surface area, measured according to the BET method, equal to or higher than 30 m$^2$/g.

4. The process according to claim 1, wherein the process further comprises, after step (b) and before step (c), a step of washing the separated precipitate, this washing being in particular performed by a protic solvent, optionally in mixture with water.

5. The process according to claim 1, wherein the process further comprises, after step (d):
   (e) heat treating the powder of the hydrated oxide of said at least one metal, leading to the powder of the anhydrous oxide of said at least one metal.

6. The process according to claim 1, wherein each metal is chosen from the group consisting of actinides, lanthanides and transition metals.

7. The process according to claim 6, wherein, when the metal is an actinide, it is chosen from a chemical element of the group consisting of U, Th, Pu, Np, Am and Cm.

8. The process according to claim 6, wherein, when the metal is a lanthanide, it is chosen from a chemical element of the group consisting of Ce, Gd, Nd, Sm and Eu.

9. The process according to claim 6, wherein, when the metal is a transition metal, it is chosen from a chemical element of the group consisting of Ti, Cr, Zr, Sc, Y and Hf.

10. The process according to claim 1, wherein when the hydrated oxide of said at least one metal is a single oxide, this oxide is chosen from the group consisting of $UO_{2+\delta}$, $UO_3$, $U_3O_8$, $CeO_{2-\delta}$, $ThO_2$, $PuO_{2-\delta}$, $NpO_{2+\delta}$, $ZrO_2$ and $HfO_2$.

11. The process according to claim 1, wherein when the hydrated oxide of said at least one metal is a mixed oxide, this oxide is chosen from the group consisting of $(U,Ce)O_{2\pm\delta}$, $(U,Pu)O_{2\pm\delta}$, $(U,Am)O_{2\pm\delta}$, $(U,Th)O_{2+\delta}$, $(Ce,Gd)O_{2-\delta}$, $(U,Gd)O_{2\pm\delta}$, $(Th,Pu)O_{2-\delta}$, $(Th,Y)O_{2-\delta}$ and $(U,Pu,Am)O_{2\pm\delta}$.

12. The process according to claim 1, wherein, for each metal, the salt of the cation of said at least one metal is chosen from the group consisting of a sulphate, nitrate, and halide.

13. The process according to claim 1, wherein the compound comprising a hydroxide is ammonium hydroxide or hydrazinium hydroxide.

14. The process according to claim 1, wherein the molar content of the compound comprising a hydroxide is in excess with respect to the total molar content of cation(s) of said at least one metal, this molar content of the compound comprising a hydroxide being between 150% and 600% with respect to the total molar content of cation(s) of said at least one metal.

15. The process according to claim 1, wherein the organic protic polar solvent is chosen from the group consisting of an alcohol, a carboxylic acid and a primary amine.

16. The process according to claim 15, wherein, when the organic protic polar solvent is an alcohol, this alcohol is a monoalcohol or a diol.

17. The process according to claim 1, wherein the vacuum drying is made by means of a vacuum manifold.

18. A powder of a hydrated oxide of at least one metal, each metal having an oxidation number between (III) and (VI), obtained by the process according to claim 1, said powder being formed by particles having an average diameter equal to or lower than 1 µm and having a specific surface area, measured according to the BET method, equal to or higher than 100 m$^2$/g; and wherein each metal is selected from the group consisting of actinides and lanthanides.

19. A process for manufacturing nuclear fuel comprising providing the powder according to claim 18 and forming a pellet from said powder suitable for utilization as nuclear fuel.

20. A process for manufacturing a pellet of an oxide of at least one metal, each metal having an oxidation number between (III) and (VI), which process comprises successively and in this order:
   (1) preparing a powder of an oxide of at least one metal, each metal having an oxidation number between (III) and (VI), by implementing the process according to claim 1,
   (2) compacting the powder, and
   (3) heat treating the compacted powder, leading to the pellet of the oxide of at least one metal.

21. The process according to claim 20, wherein the pellet of the oxide of at least one metal has a density of at least 90%.

22. The process according to claim 20, wherein the step (3) of heat treating is made by applying a temperature gradient extending from room temperature to a temperature equal to or lower than 1600° C.

* * * * *

UNITED STATES PATENT AND TRADEMARK OFFICE
CERTIFICATE OF CORRECTION

PATENT NO. : 10,347,383 B2
APPLICATION NO. : 15/110497
DATED : July 9, 2019
INVENTOR(S) : Julien Martinez et al.

It is certified that error appears in the above-identified patent and that said Letters Patent is hereby corrected as shown below:

On the Title Page

Item (73) Assignees: "Commissariat a L'Energie Atomique et al Energies Alternatives, Paris (FR)" should read --Commissariat à L'Énergie Atomique et aux Énergies Alternatives, Paris (FR)--.

Signed and Sealed this
Fifteenth Day of October, 2019

Andrei Iancu
*Director of the United States Patent and Trademark Office*